(12) United States Patent
Kosar et al.

(10) Patent No.: US 11,473,856 B2
(45) Date of Patent: Oct. 18, 2022

(54) HEAT EXCHANGER WITH ENHANCED HEAT TRANSFER SURFACES

(71) Applicant: SABANCI UNIVERSITESI, Istanbul (TR)

(72) Inventors: Ali Kosar, Istanbul (TR); Devrim Gozuacik, Istanbul (TR); Abdolali Khalili Sadaghiani, Istanbul (TR); Yunus Akkoc, Istanbul (TR); Ahmad Reza Motezakker, Istanbul (TR)

(73) Assignee: SABANCI UNIVERSITESI, Istanbul (TR)

( * ) Notice: Subject to any disclaimer, the term of this patent is extended or adjusted under 35 U.S.C. 154(b) by 369 days.

(21) Appl. No.: 16/603,599

(22) PCT Filed: Apr. 2, 2018

(86) PCT No.: PCT/TR2018/050131
§ 371 (c)(1),
(2) Date: Oct. 8, 2019

(87) PCT Pub. No.: WO2019/004967
PCT Pub. Date: Jan. 3, 2019

(65) Prior Publication Data
US 2021/0087451 A1    Mar. 25, 2021

(30) Foreign Application Priority Data

Apr. 14, 2017 (TR) .................. 2017/05596

(51) Int. Cl.
*F28F 13/18* (2006.01)
*C09D 5/00* (2006.01)
*C12N 1/20* (2006.01)

(52) U.S. Cl.
CPC .............. *F28F 13/187* (2013.01); *C09D 5/00* (2013.01); *C12N 1/20* (2013.01); *F28F 2255/20* (2013.01)

(58) Field of Classification Search
CPC ...... F28F 13/187; F28F 2255/20; C09D 5/00; C09D 7/40; C12N 1/20
(Continued)

(56) References Cited

U.S. PATENT DOCUMENTS

2003/0209340 A1    11/2003  Mcclung
2007/0230128 A1    10/2007  Kim et al.
(Continued)

FOREIGN PATENT DOCUMENTS

CN       1948886 A      4/2007
CN       101225458 A    7/2008
(Continued)

OTHER PUBLICATIONS

Archaeal Habitats-from the extreme to the ordinary Chaban et al (Year: 2008).*
(Continued)

*Primary Examiner* — Prem C Singh
*Assistant Examiner* — Francis C Campanell
(74) *Attorney, Agent, or Firm* — Bayramoglu Law Offices LLC

(57) ABSTRACT

A heat exchanger having a heat transfer surface provided with hyperthermophilic bacteria. The hyperthermophilic bacteria can be from the genera *Archaea*. The hyperthermophilic bacteria can further be from the genus *Sulfolobus*, and the hyperthermophilic bacteria can further be from the species *Sulfolobus solfataricus*. The heat exchanger can be adapted to pool-boiling heat transfer.

5 Claims, 3 Drawing Sheets

(58) Field of Classification Search
USPC .......................................................... 165/133
See application file for complete search history.

(56) References Cited

U.S. PATENT DOCUMENTS

| | | | | |
|---|---|---|---|---|
| 2014/0120601 | A1* | 5/2014 | Bywater-Ekegard | .... C12N 1/14 435/252.5 |
| 2019/0056152 | A1* | 2/2019 | Matsukuma | .............. F02C 1/04 |

FOREIGN PATENT DOCUMENTS

| | | |
|---|---|---|
| CN | 204944282 U | 1/2016 |
| CN | 206094013 U | 4/2017 |

OTHER PUBLICATIONS

Pool boiling studies on nano-structured surface by Bamerjee et al (Year: 2007).*

Chen Li, et al., Nanostructured Copper Interfaces for Enhanced Boiling. Small, 2008.4(8), pp. 1084-1088.

S.R. Sriraman, et al. Pool Boiling Studies on Nano-Structured Surfaces in ASME 2007 International Mechanical Engineering Congress and Exposition. 2007. American Society of Mechanical Engineers.

Z. Yao, et al., Pool Boiling Heat Transfer Enhancement through Nanostructures on Silicon Microchannels. Journal of Nanotechnology in Engineering and Medicine, 2012. 3(3): pp. 031002.

Terry J. Hendricks, et al., Enhancement of Pool-boiling heat transfer using nanostructured surfaces on aluminum and copper. International Journal of Heat and Mass Transfer, 2010. 53(15-16): p. 3357-3365.

Hee Seok Ahn, et al. Pool Boiling Experiments on a Nano-Structured Surface. IEEE Transactions on Components and Packaging Technologies, 2009. 32(1), pp. 156-165.

Yong Tang, et al. Pool-boiling enhancement by novel metallic nanoporous surface. Experimental Thermal and Fluid Science, 2013. 44, pp. 194-198.

Bradley Bon, et al. The Hoodoo: A New Surface Structure for Enhanced Boiling Heat Transfer. Journal of Thermal Science and Engineering Applications, 2013. 5(1), pp. 011003-011003.

K.N.Rainey, et al. Effect of Pressure, Subcooling, and Dissolved Gas on Pool Boiling Heat Transfer From Microporous Surfaces in FC-72. Journal of Heat Transfer, 2003. 125(1), pp. 75-83.

Maria Ciaramella, et al., Molecular biology of extremophiles: recent progress on the hyperthermophilic archaeon Sulfolobus. Antonie Van Leeuwenhoek, 2002. 81(1-4), pp. 85-97.

Stephen D. Bell, et al. Transcription and translation in Archaea: A mosaic of eukaryal and bacterial features. Trends in Microbiology, 1998. 6(6), pp. 222-228.

Bonnie Chaban, et al. Archaeal habitats—from the extreme to the ordinary. CAN. J. Microbiol. 2006,vol. 52, pp. 73-116, DOI: 10.1139/w05-147, J Bacteriol. Dec. 1995; 177(24): 7050-7059.

Dennis W. Grogan, Phenotypic Characterization of the Archaebacterial Genus Sulfolobus: Comparison of Five Wild-Type Strains, J Bacteriol. Dec. 1989; 171(12), pp. 6710-6719.

Ralf Moll, et al. Chemiosmotic H+ Cycling Across the Plasma Membrane of the Thermoacidophilic Archaebacterium Sulfolobus Acidocaldarius. Febs Letters. May 1988, vol. 232, No. 2, pp. 359363 10.1016/0014-5793(88)80769-5.

Kazem Kashefi, et al. Extending the Upper Temperature Limit for Life, Science, Aug. 15, 2003, vol. 301, DOI: 10.1126/science.1086823.

* cited by examiner

HEAT EXCHANGER WITH ENHANCED HEAT TRANSFER SURFACES

CROSS REFERENCE TO THE RELATED APPLICATION

This application is the national phase entry of International Application No. PCT/TR2018/050131 filed on Apr. 2, 2018, which is based upon and claims priority to Turkish Patent Application No. 2017/05596, filed on Apr. 14, 2017, the entire contents of which are incorporated herein by reference.

TECHNICAL FIELD

The present invention relates to surface enhancement in heat exchangers. More specifically, the present invention relates to a phase change heat exchanger having heat transfer surfaces coated with hyperthermophilic bacteria.

BACKGROUND

Due to latent heat at phase change, boiling corresponds to an increased amount of heat removed from surfaces of heat exchangers used in boiling heat transfer. It is generally demanded to find ways to obtain highly effective heat removal systems involving boiling heat transfer. During last decade, advances in manufacturing, nanotechnology and surface treatment engineering have led to micro/nanostructured surfaces for augmenting boiling heat transfer from heated surfaces (as in Li, C., et al., Nanostructured copper interfaces for enhanced boiling. small, 2008. 4(8): p. 1084-1088).

One of the first studies revealing the effect of nanostructured surfaces on heat transfer performance of the surface was conducted by Sriraman and Banerjee (Pool boiling studies on nano-structured surfaces. in ASME 2007 International Mechanical Engineering Congress and Exposition. 2007. American Society of Mechanical Engineers).

Yao et al. (Pool boiling heat transfer enhancement through nanostructures on silicon microchannels. Journal of Nanotechnology in Engineering and Medicine, 2012. 3(3): p. 031002) integrated nanostructures on silicon based microchannel to enhance pool boiling heat transfer. In this study, uniform silicon nanowires were used on the top, bottom and side walls of microchannels. An improvement of 120% was achieved in heat flux at a given wall superheat.

Hendricks et al. (Enhancement of pool-boiling heat transfer using nanostructured surfaces on aluminum and copper. International Journal of Heat and Mass Transfer, 2010. 53(15-16): p. 3357-3365) deposited ZnO nanostructures on Al and Cu surfaces using low temperature microreactor-assisted-nanomaterial-deposition to prepare nanostructured surfaces. 25-38° C. reductions in wall superheat was reported at a given heat flux.

Ahn et al. (Pool Boiling Experiments on a Nano-Structured Surface. IEEE Transactions on Components and Packaging Technologies, 2009. 32(1): p. 156-165) deposited multi walled carbon nanotubes (MWCNTs) on silicon wafers with different heights to improve the performance.

Dealloying is reported by Tang et al. (Pool-boiling enhancement by novel metallic nanoporous surface. Experimental Thermal and Fluid Science, 2013. 44: p. 194-198) to achieve copper nanoporous surfaces. Improvement of heat transfer and reduction in wall superheat were observed for treated surfaces compared to those of untreated surface.

Hoodoo is the name of a kind of surface structure, which was utilized by Bon et al. (The Hoodoo: A New Surface Structure for Enhanced Boiling Heat Transfer. Journal of Thermal Science and Engineering Applications, 2013. 5(1): p. 011003-011003). Hoodoo had a great effect on enhancement of boiling heat transfer, activation of nucleation sites and reaching to a critical heat flux, which imposes a limit for benefitting from boiling heat transfer.

Boiling has many industrial applications including power generation, refrigeration and cooling systems, as reported by Rainey et al. (Effect of Pressure, Subcooling, and Dissolved Gas on Pool Boiling Heat Transfer From Microporous Surfaces in FC-72. Journal of Heat Transfer, 2003. 125(1): p. 75-83). One of the main applications of pool boiling systems is cooling in fuel cells. In order to reduce $CO_2$ emission, the development of electric vehicles (EVs) has recently been accelerated. In the near future, automobiles driven by petrol or oil will be replaced by EVs or fuel cell vehicles (FCVs). In the EV power control system, an IC package is employed as electronic power equipment such as an inverter. Such IC inverters generate large amount of heat and accordingly, heat removal rates higher than 300 $W/cm^2$ can be required. High performance electronic devices including integrated circuits and logic chips generate high amount of heat. Due to the high heat removal capability, boiling is an effective method to remove high amount of heat flux from the surface followed by the control of the operating temperature of the device.

In short, surfaces offer enhanced boiling heat transfer upon certain treatments and such surfaces have the potential for addressing high heat removal requirements in many applications including microfluidics and nanofluidics systems, cooling devices, batteries.

SUMMARY

Primary object of the present invention is to overcome the abovementioned shortcomings of the prior art.

Another object of the present invention is provision of heat transfer surfaces enabling enhanced heat removal in boiling of a heated liquid.

The present invention proposes a heat exchanger with a heat transfer surface provided with hyperthermophilic bacteria, which can be from the genera *Archaea*, which can further be from the genus *Sulfolobus*, and which can further be from the species *Sulfolobus solfataricus*. The heat exchanger can be adapted to pool-boiling heat transfer.

BRIEF DESCRIPTION OF THE DRAWINGS

The figures, whose brief explanation are herewith provided, are solely intended for providing a better understanding of the present invention and are as such not intended to define the scope of protection or the context in which said scope is to be interpreted in the absence of the description.

DETAILED DESCRIPTION OF THE EMBODIMENTS

Referring now the figures outlined before, the present invention proposes a heat exchanger with a heat transfer surface provided with hyperthermophilic bacteria, which is preferably from the genera *Archaea*, more preferably from the genus *Sulfolobus*, and even more preferably from the species *Sulfolobus solfataricus*. The heat exchanger is preferably adapted to pool-boiling heat transfer.

The present invention proposes employment of *Archaea* coatings on heat exchanger surfaces for performance enhancement in pool boiling heat transfer. This type of coating is organic and biocompatible and is also adaptable to different applications, where performance enhancement is sought.

*Archaea* are known as one of the three main domains of life, and it is also divided into five phyla. Archeal cells have similar characteristics as eubacteria such as unicellular morphology. They have a circular chromosome and resemble to eukaryotic cells due to the their metabolisms such as DNA replication and transcription (Ciaramella et al., Molecular biology of extremophiles: recent progress on the hyperthermophilic archaeon *Sulfolobus*. Antonie Van Leeuwenhoek, 2002. 81(1-4): p. 85-97; Bell and Jackson, Transcription and translation in *Archaea*: A mosaic of eukaryal and bacterial features. Trends in Microbiology, 1998. 6(6): p. 222-228). Archeal cells have very unique survival ability under physiologically harsh conditions such as low or high temperatures (e.g. between −2° C. to 15° C. or between 60° C. to 122° C.), high salinity (such as 2M to 5M of NaCl) and extreme pH values (lower than 4 and also higher than 9) (DOI: 10.1139/w05-147; J Bacteriol. 1995 December; 177(24): 7050-7059; and DOI: 10.1126/science.1086823).

Hyperthermophilic archeon called *Sulfolobus solfataricus* belongs to the phylum Crenarchaeota. It was first isolated from *Pisciarelli Solfatara* in Italy (10.1016/0014-5793(88) 80769-5). *Sulfolobus solfataricus* is an irregular and lobe-shaped archaeon having a size about 0.2 to 2 µm, grows optimally at 80-85° C. and has a pH of around 3 while maintaining intracellular pH around 6.5 and can utilize variable carbon sources to maintain cellular homeostasis (J Bacteriol. 1989 December; 171(12): 6710-6719). This robust and heat resistant microorganism is a good candidate for organic industrial coating purposes, which constitutes the motivation behind the invention.

Experimental Setup

Figure 1:
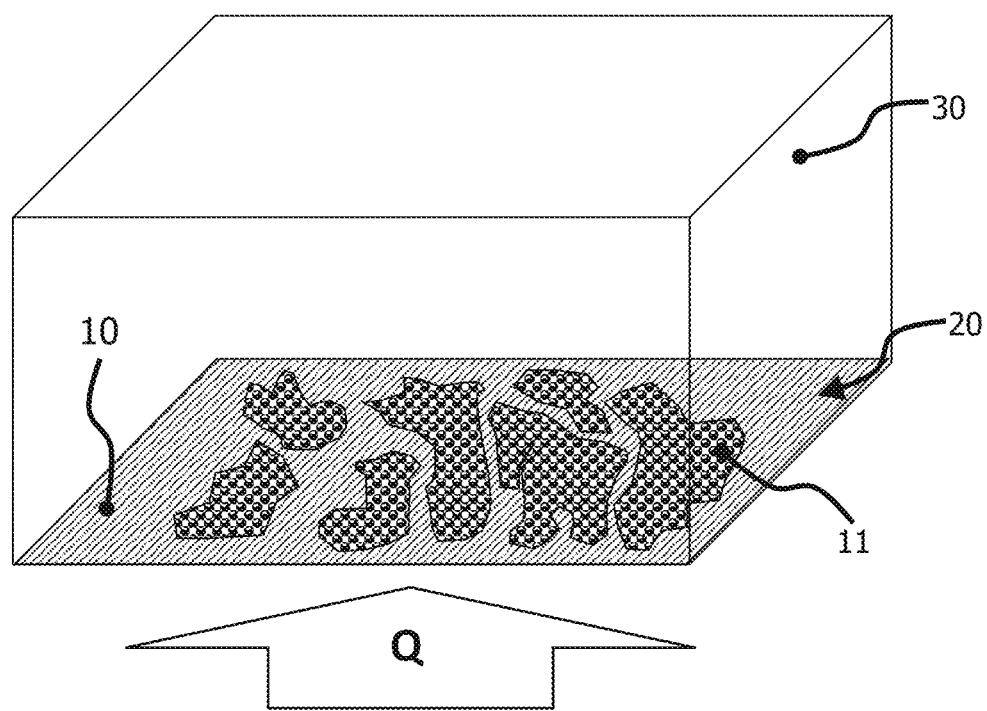
FIG. 1 schematizes an exemplary pool boiling experimental setup for testing the performance of the coating in heat removal from its heat transfer surfaces.

An exemplary pool boiling experimental setup for testing the performance of the coating in heat removal from its heat transfer surfaces, is schematicized in FIG. 1. The setup is designed to imitate a heat exchanger having a heat transfer surface which requires high heat fluxes such as those to be cooled using pool boiling.

The setup comprises a heating surface (10) on a conductive body (20) which can be in form of a plate, preferably comprising a material with high heat transfer coefficient such as metals e.g. aluminium. The setup can be provided with thermocouples, cartridge heaters, gasket sealers and a reflux condenser (none shown).

The setup can comprise a receptacle (30) for holding a liquid to be boiled. The conductive body (20) can have holes for inserting one or more heater such as cartridge heaters, which can at least partly cover a side of the conductive body, mainly perpendicular to an intended heat flow direction for provision of heat (referred to as "Q" in the FIG. 1).

The conductive body (20) can further comprise holes (not shown) for temperature measurement device(s) (not shown), such as thermocouples located at said side of the conductive body. The heater(s) can be press-fitted into the holes, while conductive silicon grease can be utilized to fill gaps between heaters and the inner walls of the holes.

Holding means (not shown) such as holder plates can be used to restrict the positions of the receptacle (30) and the heater(s) relative to each other. An upper side of the setup can comprise one or more hole or conduit for filling up the receptacle (30) with fluid, for inserting a thermocouple (not shown) to measure bulk temperature of the fluid (not shown), and for connecting a condenser (e.g. a reflux condenser, not shown) to the receptacle (30) for condensing and returning boiled fluid back into the receptacle (30).

Gasket sealers resistant to high temperatures can be used between the edges of the receptacle (30), edges of the heater(s) and of the upper plates to prevent any leakage as well as between the heater and holding means to prevent heat dissipation. Any gap between outer and inner tubes of the condenser can be filled with a fluid (e.g. water) to condense vapor escaping through the inner tube, which can be open to atmosphere to keep the process under atmospheric pressure.

The volume of liquid in the receptacle (30) was measured before and after each test to monitor the amount of liquid used in pool boiling experiments. It was observed that a vertical reflux condenser as described above was efficient and the amount of water remained nearly the same after each experiment. Current and voltage used in energizing the heater can be adjusted using a digital power supply (not shown) with multimeters, which can nowadays provide high precision. The power supply can be directly connected to heaters, e.g. cartridge heaters. All of the fluid and surface (10) temperatures and power readings were recorded under steady state conditions. To make sure about the repeatability, each experiment was repeated for several times.

*Archaea* Employed in the Experimental Setup

The main characteristics of biocoated surfaces is observed to be that they provide numerous active nucleation sites (11), from where a high number of bubbles can emerge and depart from the surfaces, and this corresponds to an enhanced heat transfer to the fluid due to removal of phase change heat. Thus, according to the close relation between the surface structures and the number of the active nucleation sites (11), the inventors first examined the structure of *Sulfolobus solfataricus* colonies under fluorescent microscopy either with visible or fluorescent light. Archeae colonies (corresponding to the active nucleation sites 11) were obtained under sustained optimal conditions and then a sample of the culture medium was examined under microscopy using DAPI (4', 6-diamidino-2-phenylindole) as staining. The SEM (Scanning Electron Microscopy) images of coated and uncoated surfaces were also obtained, wherein zones coated with bacteria can be distinguishably visualized.

Boiling Heat Transfer Experiments

Figure 2B:
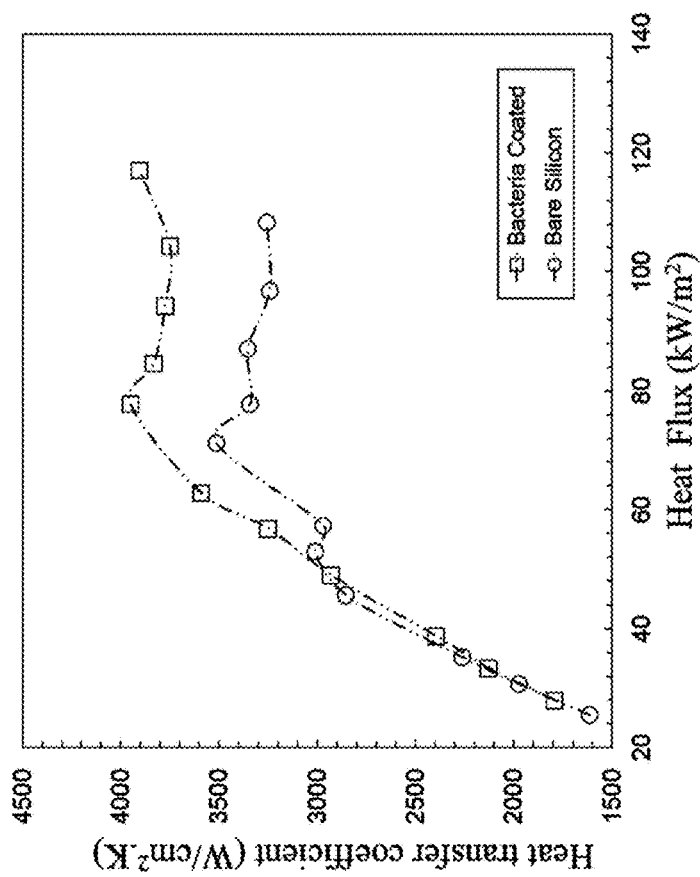
FIG. 2B shows comparative graphs of heat flux vs. heat transfer coefficient values obtained from bare Silicon surfaces and biocoated surfaces on a heat exchanger according to the present invention.
Figure 2A:
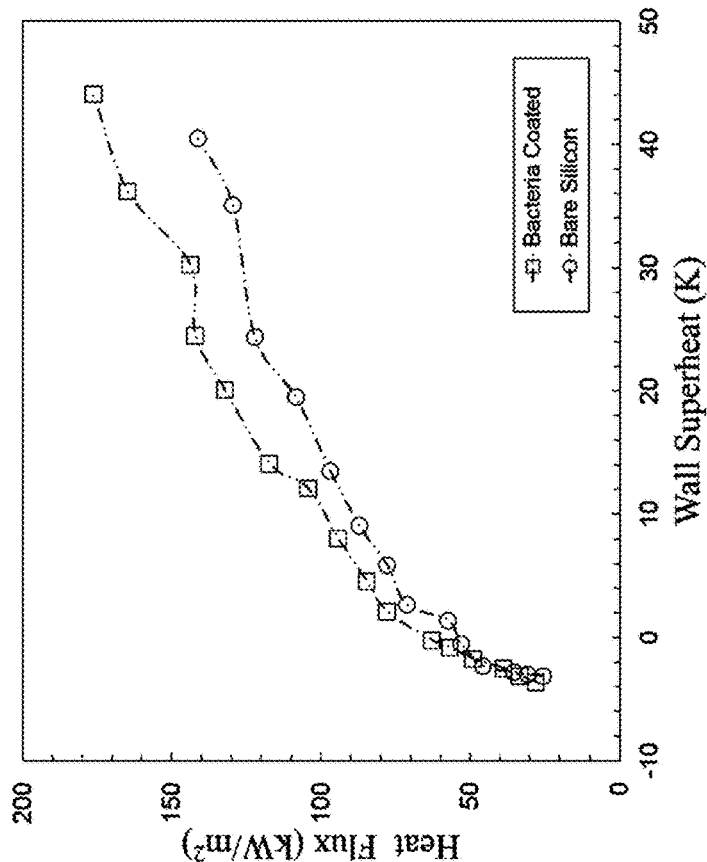
FIG. 2A shows comparative graphs of wall superheat vs. heat flux, values obtained from bare Silicon surfaces and biocoated surfaces on a heat exchanger according to the present invention.

Wall superheat (difference between wall temperature and saturation temperature) and heat transfer coefficients for hyperthermophylic bacteria (here: *archaea*) coated and bare silicon surfaces are shown in FIG. 2A and FIG. 2B. According to the test results, heat transfer enhancement using bacteria coated surfaces was 20% higher relative to uncoated surfaces.

Figure 3A:
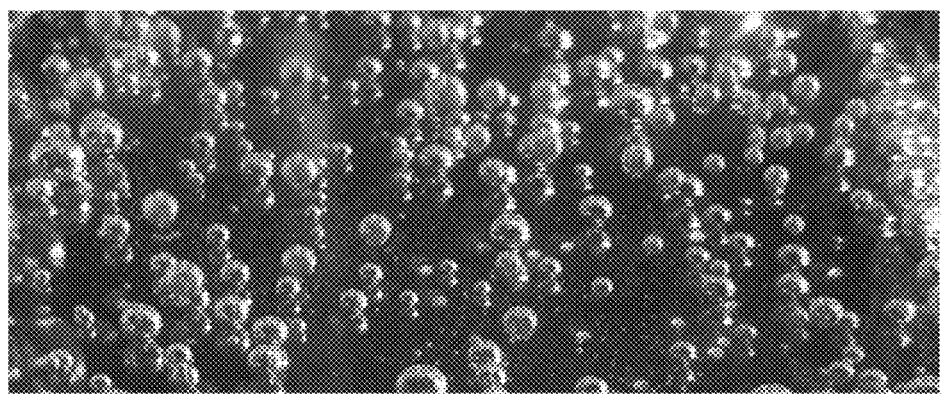
FIG. 3A shows bubbles generation at boiling on bare/uncoated surfaces.
Figure 3B:
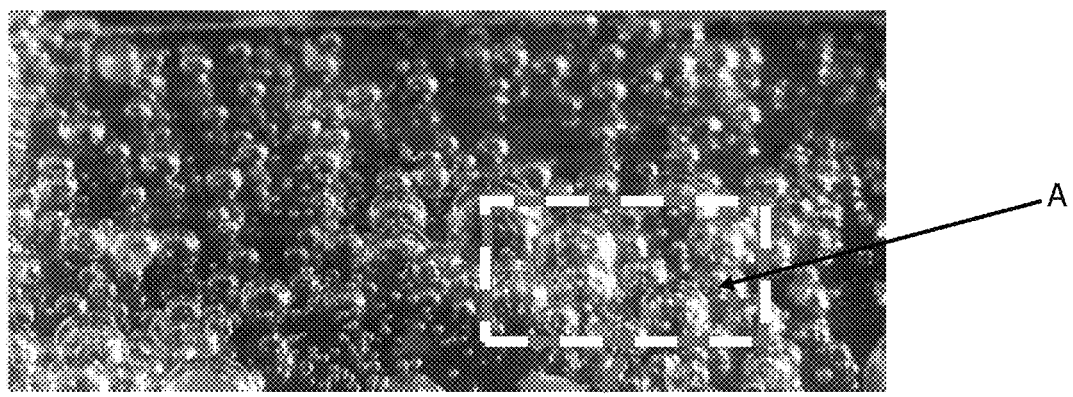
FIG. 3B shows bubbles generation at boiling on surfaces partly coated with *Archaea* colonies.
Figure 3C:
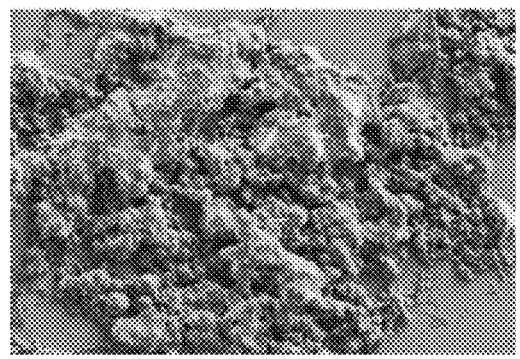
FIG. 3C shows SEM photograph of *Archaea* colony coated on a heat transfer surface portion A emphasized in FIG. 3B.

Generated bubbles from bare silicon and *Archaea* coated samples are shown in FIGS. 3A-3C. Due to the porous structure of the bacteria, the coated surfaces have much more active nucleation sites (11) in comparison to the bare silicon surface. Bubble dynamics on coated and uncoated surfaces was visualized and analyzed using a high speed camera.

Accordingly, the inventors have found an increase in active nucleation site density (number of sites that bubble generate and merge) at biocoated regions with *Archaea* colonies leading to heat transfer enhancement, and bubble interaction during the departure emerged as an important factor. The bubbles on biocoated surface portions emerge and grow to a full size more rapidly then on uncoated surface portions, and therefore leave the heat transfer surface earlier. This agitation causes further liquid displacement in the vicinity of the biocoated surface portions, thus enhances the temperature gradient and further enhances the convective heat transfer coefficient around said portions.

Many surface enhancement techniques such as pin-fin arrays, reentrant cavities, and surface treatments increasing porosity are already available in the literature for conventional size tubes. As the tube size shrinks and round geometries restricting the use of conventional microfabrication methods are used, limited surface enhancement methods could be implemented.

Biocoatings including hyperthermophilic bacteria, such as *Archaea* coatings exemplified in the present description, could offer a significant alternative and even improvement to surface enhancements in microchannels/tubes as well as conventional scale, since the implementation is easy, cost efficient, less dependent on surface shape and organic. The biocoating can be also easily used on closed geometries such as microtubes, where physical deposition techniques are not applicable.

Metal surfaces comprising Al or Fe mainly found in form of their oxides reside positive charges on their surfaces. Many organic molecules reside carboxyl and amine groups, which are negatively and positively charged, respectively. The coating used in the present invention changes the net charge of the surface. *Archaea* have hydrophobic regions on their surfaces and like the charges, hydrophobicity of a surface (such as a metal surface as mentioned above) may be manipulated by application of *archaea* coatings thereon. Thus, the coating used in the present invention further provides combinatory solutions, against the problems which other conventional coating materials fail.

Due to the porous structure, surfaces coated with hyperthermophilic bacteria (here: *archaea*) have much more active nucleation sites (11) in comparison to the bare surfaces and therefore have higher pool boiling heat transfer performance. Such coating also provides enhanced heat transfer surface area which further improves heat transfer rates. Such biocoatings further have the potential of offering biocompatibility. Sulfur acts as the final electron acceptor rather than oxygen in the respiration of the archea named *Sulfolobus solfataricus*. Metabolically, *Sulfolobus solfataricus* depends on these sulfur containing compounds to produce energy either heterotrophic or autotrophic. The use of *Sulfolobus solfataricus* in coating of metal surfaces in combustion engines might simultaneously reduce the release of the Sulfoxides emerged by the course of combustion, which further advantage can be classified as biodesulfurization or microbial desulfurization.

Thus the following objects are achieved by the present invention:
overcoming the abovementioned shortcomings of the prior art,
provision of heat transfer surfaces enabling enhanced heat removal at boiling of a heated liquid.

LIST OF REFERENCE SIGNS 10 heating surface
11 active nucleation site
20 conductive body
30 receptacle
Q intended heat flow direction

What is claimed is:

1. A heat exchanger comprising a heat transfer surface coated with hyperthermophilic bacteria from species *Sulfolobus solfataricus*, wherein the hyperthermophilic bacteria form active nucleation sites on the heat transfer surface.

2. The heat exchanger according to claim 1, wherein, the heat exchanger is adapted to pool-boiling heat transfer.

3. The heat exchanger according to claim 1, wherein the hyperthermophilic bacteria on the heat transfer surface form a porous structure.

4. The heat exchanger according to claim 1, wherein the hyperthermophilic bacteria on the heat transfer surface have a size of 0.2 to 2 μm.

5. The heat exchanger according to claim 1, wherein the hyperthermophilic bacteria on the heat transfer surface are irregular and lobe-shaped.

* * * * *